United States Patent
Liu

(10) Patent No.: US 9,301,548 B2
(45) Date of Patent: *Apr. 5, 2016

(54) ELECTRONIC CIGARETTE

(75) Inventor: Qiuming Liu, Shenzhen (CN)

(73) Assignee: HUIZHOU KIMREE TECHNOLOGY CO., LTD. SHENZHEN BRANCH, Shenzhen, Guangdong Province (CN)

( * ) Notice: Subject to any disclaimer, the term of this patent is extended or adjusted under 35 U.S.C. 154(b) by 612 days.

This patent is subject to a terminal disclaimer.

(21) Appl. No.: 13/703,017

(22) PCT Filed: Jul. 23, 2012

(86) PCT No.: PCT/CN2012/079036
§ 371 (c)(1),
(2), (4) Date: Dec. 8, 2012

(87) PCT Pub. No.: WO2014/015461
PCT Pub. Date: Jan. 30, 2014

(65) Prior Publication Data
US 2014/0020696 A1 Jan. 23, 2014

(51) Int. Cl.
*A24F 47/00* (2006.01)
*A61M 15/06* (2006.01)

(52) U.S. Cl.
CPC ............. *A24F 47/008* (2013.01); *A24F 47/002* (2013.01); *A61M 15/06* (2013.01)

(58) Field of Classification Search
CPC ..... A24F 47/00; A24F 47/002; A24F 47/004; A24F 47/006; A24F 47/008; A61M 15/06
See application file for complete search history.

(56) References Cited

U.S. PATENT DOCUMENTS

| 7,351,066 | B2 * | 4/2008 | DiFonzo et al. | 439/39 |
| 8,973,587 | B2 * | 3/2015 | Liu | 131/273 |
| 9,080,734 | B2 * | 7/2015 | Andersen et al. | |
| 2005/0255718 | A1 * | 11/2005 | McLeish | 439/39 |
| 2007/0178771 | A1 * | 8/2007 | Goetz et al. | 439/669 |
| 2013/0152922 | A1 * | 6/2013 | Benassayag et al. | 128/202.21 |
| 2013/0220315 | A1 * | 8/2013 | Conley et al. | 128/202.21 |
| 2013/0255702 | A1 * | 10/2013 | Griffith et al. | 131/328 |

* cited by examiner

*Primary Examiner* — Anthony Calandra
(74) *Attorney, Agent, or Firm* — Cheng-Ju Chiang

(57) ABSTRACT

An electronic cigarette comprises a smoking unit and a power unit. The smoking unit attachably connects with the power unit as a unitary member by magnetism. A connecting end of the smoking unit and a corresponding connecting end of the power unit respectively comprise a connecting element which is made of iron material. A permanent magnet is disposed in at least one of the connecting end of the smoking unit and the corresponding end of the power unit. The connecting element of the connecting end of the smoking unit and the connecting element of the corresponding connecting end of the power unit are removably and insertedly connected to each other, and engaged with each other via an attractive force of the permanent magnet. The electronic cigarette can be assembled and disassembled conveniently and efficiently, and is easy for maintenance and replacement.

14 Claims, 9 Drawing Sheets

ELECTRONIC CIGARETTE

CROSS REFERENCE TO RELATED APPLICATIONS

The present application is a 35 U.S.C. §371 National Phase conversion of International (PCT) Patent Application No. PCT/CN2012/079036, filed on Jul. 23, 2012, the disclosure of which is incorporated by reference herein. The PCT International Patent Application was filed in Chinese.

TECHNICAL FIELD

The present invention relates to an electronic cigarette, and especially to an electronic cigarette using magnetism for attachment and connection thereof.

DESCRIPTION OF BACKGROUND

Current electronic cigarettes comprise an inhaling rod and a power rod. The inhaling rod comprises a smoke liquid cup used to store smoke liquid and an atomizer used to atomize the stored smoke liquid and to turn it into smoke. The power rod comprises a battery for powering the atomizer to work. The inhaling rod and the power rod are threadedly connected. It is inconvenient and time consuming to connect the inhaling rod with the power rod by screw thread. Besides, the internal structure of the current inhaling rod is complex so that it is inconvenient to maintain and replace the atomizer. In addition, the internal structure of the smoke liquid cup is complex since it is structurally independent.

SUMMARY

An object of the present invention is to provide an electronic cigarette which is easy to assemble, disassemble, maintain and replace.

To achieve the above objects, the present invention provides an electronic cigarette comprising a smoking unit and a power unit, wherein the smoking unit attachably connects with the power unit as a unitary member by magnetism.

Furthermore, a connecting end of the smoking unit and a corresponding connecting end of the power unit respectively comprise a connecting element which is made of iron material. A permanent magnet is disposed in at least one of the connecting end of the smoking unit and the corresponding end of the power unit. The connecting element of the connecting end of the smoking unit and the connecting element of the corresponding connecting end of the power unit are removably and insertedly connected to each other, and engaged with each other via an attractive force of the permanent magnet.

Furthermore, ends of the two connecting elements are attracted to each other and one of the ends of the two connecting elements abuts against a top of the permanent magnet. A bottom of the permanent magnet is supported by a flexible element. The permanent magnet is configured to be fixed in the connecting end of the smoking unit or the corresponding end of the power unit by an iron fixing sheath.

Furthermore, the connecting elements are both substantially cylindrical and the permanent magnet is a ring structure. A first battery electrode is insertedly disposed in a center of the ring structure of the permanent magnet and an insulator is disposed between the first battery electrode and the permanent magnet.

Furthermore, the connecting element of the corresponding connecting end of the power unit is a female connecting element. Correspondingly, a male connecting element is the connecting element of the connecting end of the smoking unit. The permanent magnet is disposed in the corresponding connecting end of the power unit.

Furthermore, the female connecting element is fixed at the corresponding connecting end of the power unit via the iron fixing sheath which is insertedly installed at an inner wall of the corresponding connecting end of the power unit, and the permanent magnet is fixed in the fixing sheath.

Furthermore, the fixing sheath is cylindrical, and comprises a sidewall, a bottom wall, and an inner chamber formed and surrounded by the sidewall and the bottom wall. The fixing sheath is snugly secured at an inner wall of the corresponding connecting end of the power unit via an outer wall of the fixing sheath. A positioning step of the fixing sheath is formed at an inner wall of the fixing sheath for supporting the permanent magnet which is installed in the inner chamber of the fixing sheath and is supported on the positioning step of the fixing sheath. The female connecting element is inserted in the inner chamber of the fixing sheath and engages with the permanent magnet to fix the permanent magnet. The bottom wall of the fixing sheath comprises a through hole. The female connecting element is used as a second electrode of the power unit.

Furthermore, the female connecting element comprises a cylindrical first connecting part. A first chamber is defined inside the first connecting part in order to insertably connect and mate with the male connecting element. A positioning step of the first connecting part is disposed and extends outwardly from an outer wall of the first connecting part along a radial direction of the first connecting part in order for snugly matching with the corresponding connecting end of the power unit. The female connecting element is snugly fixed at the inner wall of the corresponding connecting end of the power unit via the outer wall of the first connecting part.

Furthermore, the female connecting element further comprises a second connecting part used to insertedly connect with the connecting end of the smoking unit. The second connecting part is cylindrical and is formed by starting from the positioning step of the first connecting part and extending away from the first connecting part along an axial direction thereof. The second connecting part communicates with the first connecting part and forms a cylindrical second chamber therein for accommodating the connecting end of the smoking unit. An inner wall of the second connecting part and an outer wall of the connecting end of the smoking unit are interferentially engaged with each other.

Furthermore, the male connecting element comprises a cylindrical upper portion and lower portion. The upper portion of the male connecting element is used to connectively engage with the connecting end of the smoking unit and the lower portion of the male connecting element is used to connectively engage with the female connecting element. A positioning step of the male connecting element is formed between the upper portion and the lower portion by extending outwards along a radial direction of the male connecting element, and is used to engage with the connecting end of the smoking unit. Besides, the positioning step of the male connecting element is used to engage with the female connecting element at the same time for restricting relative locations thereof. An engaging ring is formed at an inner wall of the lower portion for installation of a first atomizing electrode of the smoking unit. The first atomizing electrode of the smoking unit is secured in the engaging ring via an insulating piece. A vent is formed at a center of the smoking unit and penetrates through the smoking unit along an axial direction thereof, and the male connecting element is used as a second atomizing electrode of the smoking unit.

Furthermore, a fixation hole is formed at a center of the permanent magnet and is used to install the first battery electrode of the power unit therein which is fixed in the fixation hole via an insulator.

Furthermore, the first battery electrode is substantially cylindrical. A circular positioning step of the first battery electrode is formed at a central periphery of the first battery electrode and separates the first battery electrode into an electrode upper portion and an electrode lower portion. The second insulator is sheathingly installed outside the electrode upper portion of the first battery electrode, and is snugly inserted and fixed in the fixation hole of the permanent magnet together with the upper portion. An end of the second insulator engages with a top surface of the positioning step for positioning in order to fix the first battery electrode and the permanent magnet. An electrode vent is further formed and penetrates through the first battery electrode along an axial direction thereof.

Furthermore, the electrode lower portion of the power unit is electrically insulated from the fixing sheath via an insulating pad which is disposed at the bottom wall of the fixing sheath, and a central through hole is formed at a center of the insulating pad and penetrates through the insulating pad along an axial direction thereof.

Furthermore, the flexible element is sheathingly installed at an outer wall of the electrode lower portion of the first battery electrode of the power unit. Both ends of the flexible element respectively engage with the positioning step of the first battery electrode and the insulating pad. A pressing force generated by constricting the flexible element makes the first battery electrode of the power unit being held and secured in the second insulator and unable to be loose and to further make the permanent magnet elastically engaging with the female connecting element.

Furthermore, the electrode lower portion of the first battery electrode of the power unit penetrates respectively through the central through hole of the insulating pad and the through hole of the fixing sheath, and extends out of the bottom wall of the fixing sheath.

According to the electronic cigarette of the present invention, the smoking unit attachably connects with the power unit as a unitary member by magnetism. A connecting end of the smoking unit and a corresponding connecting end of the power unit respectively comprise a connecting element which is made of iron material. A permanent magnet is disposed in at least one of the connecting end of the smoking unit and the corresponding end of the power unit, and the connecting element of the connecting end of the smoking unit and the connecting element of the corresponding connecting end of the power unit are removably and insertedly connected to each other, and engaged with each other via an attractive force of the permanent magnet. This structure of the electronic cigarette is convenient and efficient to assemble and disassemble. Besides, the atomizer is installed in the smoke liquid reservoir via a conduit and an inhaling cover itself is further used as an assembly part of the smoke liquid reservoir. Such structure as above makes the whole structure of the smoking unit much compact and simple.

Embodiments of the present invention are further described in detail in cooperation with drawings as follows.

DETAILED DESCRIPTION OF THE EMBODIMENTS

Figure 1:
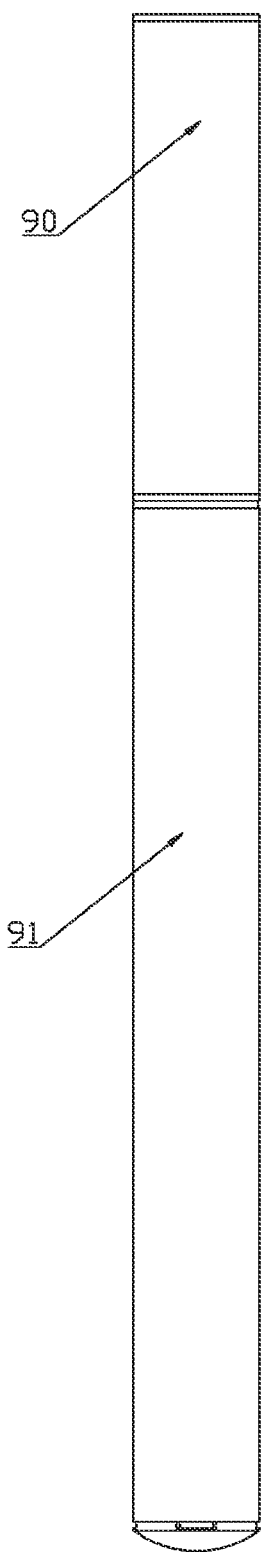
FIG. 1 is an elevation view of an electronic cigarette in accordance with the first embodiment of the present invention.

As shown in FIGS. 1-11, an electronic cigarette 100 is provided in accordance with a first embodiment of the present invention. The electronic cigarette 100 comprises an electronic cigarette smoking unit 90 and a power unit 91. The smoking unit 90 attachably connects with the power unit 91 as a unitary member by magnetism.

A connecting end of the smoking unit 90 and a corresponding connecting end of the power unit 91 respectively comprise a connecting element 5 or 911 which is made of iron material. A permanent magnet 8 is disposed in at least one of the connecting end of the smoking unit 90 and the corresponding connecting end of the power unit 91. The connecting element 5 of the connecting end of the smoking unit 90 and the connecting element 911 of the corresponding connecting end of the power unit 91 are removably and insertedly connected with each other, and engaged with each other via an attractive force of the permanent magnet 8. Ends of the two connecting elements 5, 911 are attracted to each other and one of the ends of the two connecting elements 5, 911 abuts against a top of the permanent magnet 8. A bottom of the permanent magnet 8 is supported by a flexible element 917. The permanent magnet 8 is configured to be fixed in the connecting end of the smoking unit 90 or the corresponding connecting end of the power unit 91 by an iron fixing sheath 914. The connecting elements 5, 911 are substantially cylindrical and the permanent magnet 8 is a ring structure. A first battery electrode 915 is insertedly disposed in a center of the ring structure of the permanent magnet 8, and an insulator 916 is disposed between the first battery electrode 915 and the permanent magnet 8. Understandably, the connecting elements 5, 911 can be independent parts from the smoking unit 90 or the power unit 91, or be integrally structural parts with the smoking unit 90 or the power unit 91. The fixing sheath 914 can be an independent part from the smoking unit 90 or the power unit 91, or be an integrally structural part with the smoking unit 90 or the power unit 91.

In this embodiment, the electronic cigarette smoking unit 90 comprises an inhaling cylinder 1, an atomizing device 2, a smoke liquid reservoir 3, an inhaling cover 4 and a male connecting element 5 used to connect with the power unit 91. The inhaling cover 4 and the male connecting element 5 are respectively disposed at two ends 11, 12 of the inhaling cylinder 1, and the inhaling cylinder 1 accommodates the atomizing device 2 and the smoke liquid reservoir 3 therein. In this embodiment, the above mentioned two connecting elements are respectively the male connecting element 5 which is disposed at the smoking unit 90 and a female connecting element 911 which is disposed at the power unit 91 as described below.

Figure 2:
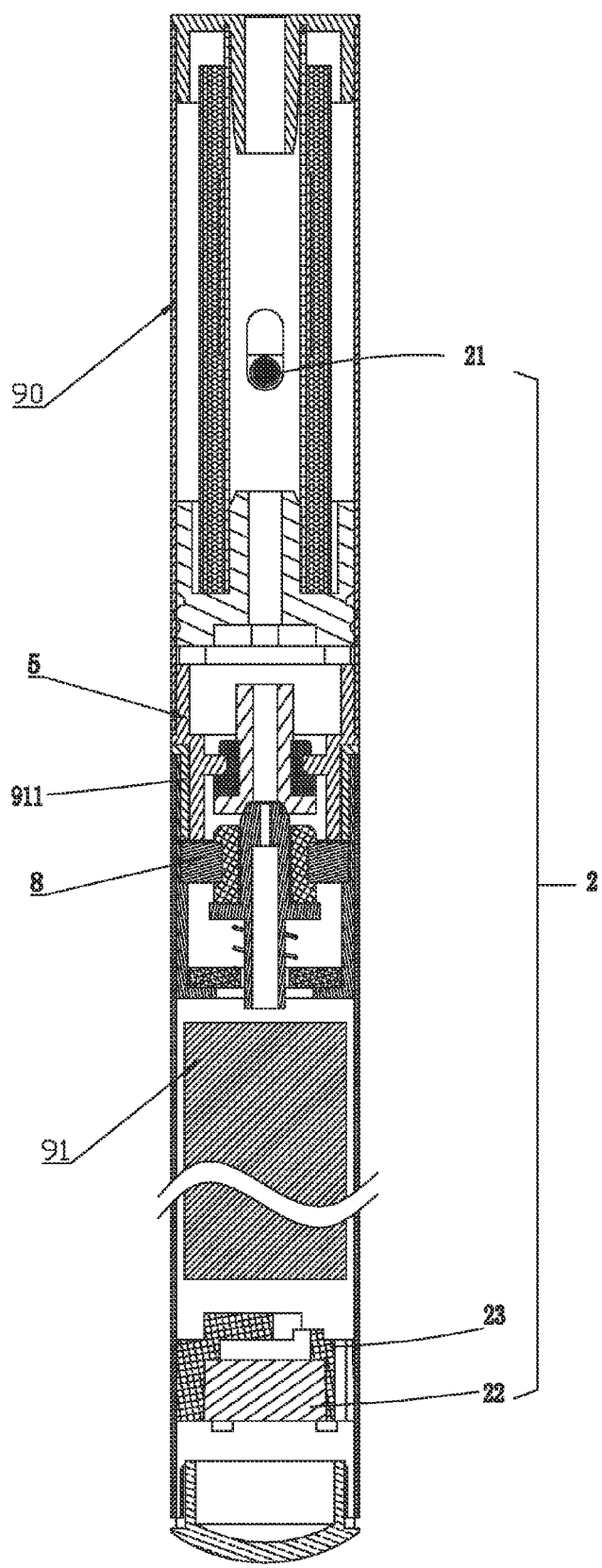
FIG. 2 is a cross-sectional view of an electronic cigarette in accordance with the first embodiment of the present invention.

The inhaling cylinder 1 is a hollow cylindrical structure, especially in this embodiment, a cylindrical casing which is made of transparent or translucent plastic material, or made as a metal casing. Along a depicting orientation as shown in FIG. 2, the inhaling cylinder 1 comprises a first end 11 which connects the inhaling cover 4 and a second end 12 which connects the power unit 91. The first end 11 installs the above mentioned inhaling cover 4 and the second end 12 installs the above mentioned male connecting element 5. A first atomizing electrode 13 (such as a negative electrode) of the atomizing device 2 and a first insulating piece or ring 14 are disposed at the second end 12 of the inhaling cylinder 1, and a vent is disposed at a center of the first atomizing electrode 13 of the atomizing device 2. In this embodiment, the male connecting element 5 is used as a second atomizing electrode (such as a positive electrode) of the atomizing device 2.

As shown in FIGS. 2-6, the atomizing device 2 comprises an atomizer 21, an atomizer control circuit board 22 and a circuit board fixing base 23 for accommodating and fixedly securing the atomizer control circuit board 22 therein. In this embodiment, the atomizer 21 is installed in the inhaling cylinder 1, and the atomizer control circuit board 22 and the circuit board fixing base 23 are disposed in the power unit 91. The atomizer control circuit board 22 comprises a micropneumatic switch thereon to control electrical connection of related circuits for allowing the atomizer 21 to initiate for work.

Figure 3:
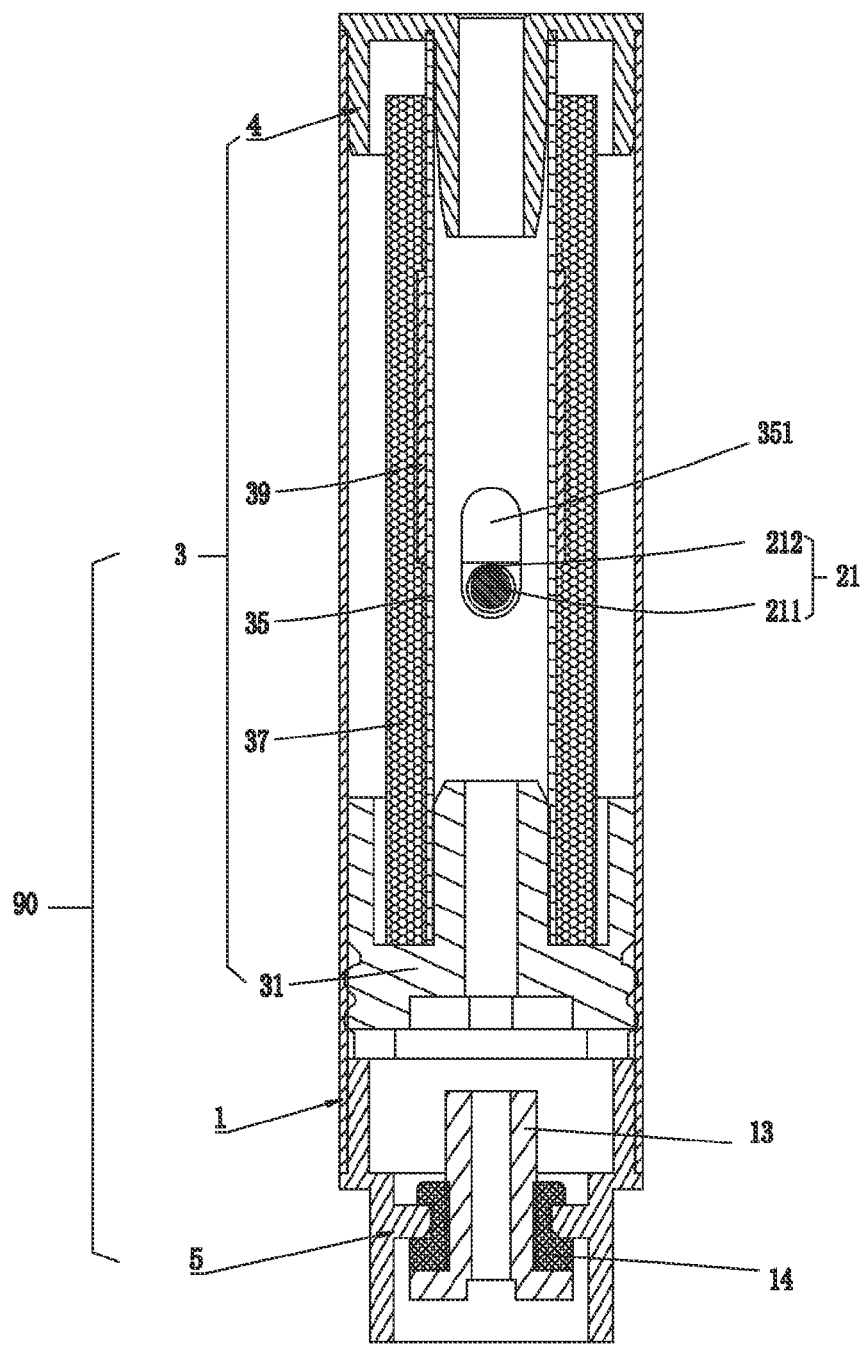
FIG. 3 is a cross-sectional view of a smoking unit of an electronic cigarette in accordance with the first embodiment of the present invention.

As shown in FIG. 3, the atomizer 21 atomizes smoke liquid for turning the smoke liquid into smoke. The atomizer 21 comprises a heating wire 211, and a fiber element 212 used for absorbing the smoke liquid and supporting the heating wire 211. The heating wire 211 entwines around the fiber element 212. The fiber element 212 is able to work like a sponge for absorbing and storing water/liquid therein, and is able to be made of glass fiber or any materials like cotton material capable of absorbing and isolating liquid. In this embodiment, the fiber element 212 is accommodated and fixed in the smoke liquid reservoir 3, and two ends of the heating wire 211 penetrate through and out of the smoke liquid reservoir 3 to further electrically connect with a positive electrode and a negative electrode in the power unit 91.

Figure 4:
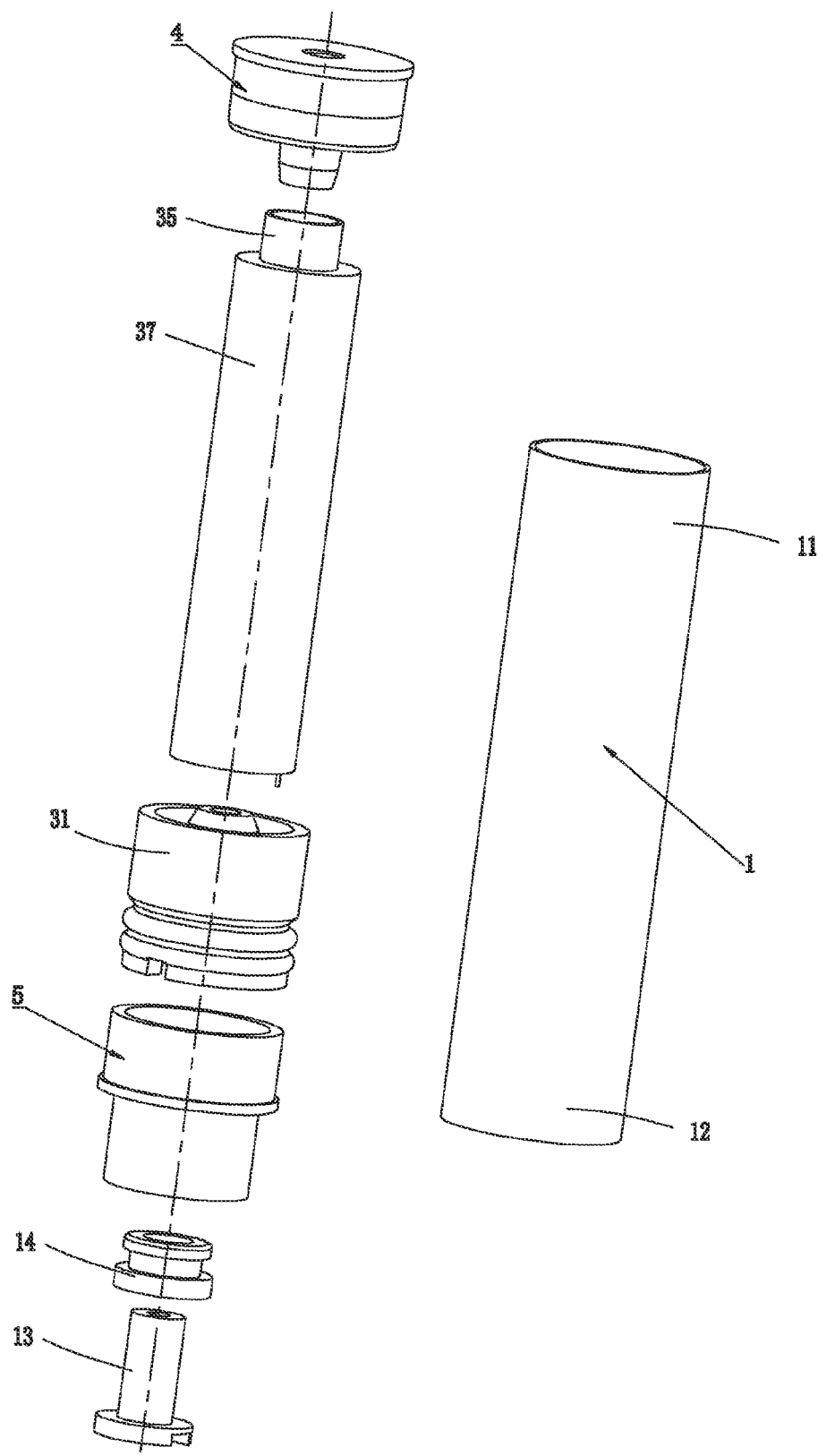
FIG. 4 is an exploded view of a smoking unit of an electronic cigarette in accordance with the first embodiment of the present invention.

As shown in FIGS. 3-4, in this embodiment, the smoke liquid reservoir 3 comprises a seat 31, the inhaling cover 4, a conduit 35, a liquid accumulator 37 and a positioning tube 39 used to prevent the atomizer 21 from moving along an axial direction of the electronic cigarette smoking unit 90. Especially, the seat 31 and the inhaling cover 4 are spaced from and face each other in a particular interval and are fixed onto an inner wall of the inhaling cylinder 1. The conduit 35 is fixedly disposed between the seat 31 and the inhaling cover 4, and the liquid accumulator 37 is fixed outside the conduit 35 and is located between the seat 31 and the inhaling cover 4. The positioning tube 39 is sheathingly installed onto an outer wall of the conduit 35 and engages with the atomizer 21.

Figure 8:
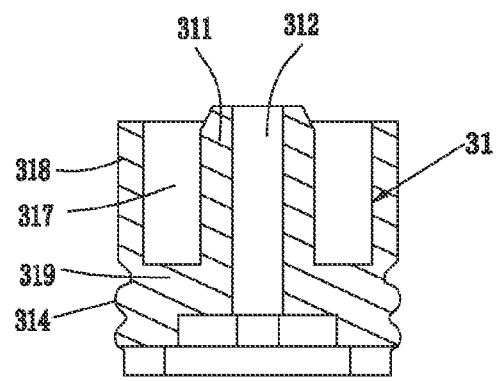
FIG. 8 is a cross-sectional view of a seat of a smoke liquid reservoir of an electronic cigarette in accordance with the first embodiment of the present invention.

In this embodiment, the seat 31 (as shown in FIG. 8) is a cylindrical cup body, and comprising an annular sidewall 318, a circular cup base 319 and a positioning column 311 extending from a center of the cup base 319 along an axial direction of the seat 31. An annular inner chamber 317 is defined between the annular sidewall 318 and the positioning column 311. A seat vent 312 is formed by penetrating through the positioning column 311 and the cup base 319 along the axial direction, and the cup base 319 comprises two penetrating threading holes (not shown) for the heating wire 211 to perforate therethrough. A snug ring 314 is installed outside the sidewall 318 to snugly engage with the inhaling cylinder 1. The seat 31 is snugly fixed at the inner wall of the inhaling cylinder 1 by snugness of the sidewall 318 and the snug ring 314.

The inhaling cover 4 (referring to FIG. 7) is able to be made of silica gel materials, and its shape and size fit with the inner wall of the inhaling cylinder 1. In this embodiment, the inhaling cover 4 is a cylindrical cover body, and comprises an outer annular sidewall 48, a top wall 49, and a positioning column 41 which extends from a center of the top wall 49 along in an axial direction of the inhaling cover 4. An annular inner chamber 47 is defined by and between the positioning column 41 and the sidewall 48. The inhaling cover 4 further comprises an inhaling-cover vent 42 which penetrates through the positioning column 41 and the top wall 49 along the axial direction of the inhaling cover 4, and a positioning step 43 which radially extends outwards to engage with the first end 11 of the inhaling cylinder 1. An outer diameter of the inhaling cover 4 is slightly larger than an inner diameter of the inhaling cylinder 1, and as a result, the inhaling cover 4 is able to be snugly secured at the inner wall of the inhaling cylinder 1 via the sidewall 48 thereof. The inhaling cover 4 is ready to be pulled out for continuously refilling smoke liquid into the smoke liquid reservoir 3 when the smoke liquid is used up in the smoke liquid reservoir 3. The positioning column 41 of the inhaling cover 4 corresponds to the positioning column 311 of the seat 31, and the positioning column 41 of the inhaling cover 4 and the positioning column 311 of the seat 31 are respectively secured at two ends of the conduit 35. The annular inner chamber 47 of the inhaling cover 4 corresponds to the annular inner chamber 317 of the seat 31, and the annular inner chamber 47 of the inhaling cover 4 and the annular inner chamber 317 of the seat 31 are used to respectively accommodate two ends of the liquid accumulator 37.

The conduit 35 (as shown in FIG. 3) is used to support the liquid accumulator 37, in the meantime control a height of the smoke liquid reservoir 3 and support the fiber element 212, and is also used to serve as a passageway to move toward an outside of the inhaling cylinder 1 for smoke which is generated after the smoke liquid is atomized into smoke by the atomizing device 2. In this embodiment, the conduit 35 is a hollow tube which is able to be made of plastic or fiber materials, such as a glass fiber tube. The conduit 35 comprises a top and a bottom. The top is sheathingly installed onto the positioning column 41 of the inhaling cover 4 to sealedly connect with a periphery thereof, and the bottom is sheathingly installed onto the positioning column 311 of the seat 31 to sealedly connect with a periphery thereof. The conduit 35 forms a notch 351 which penetrates through a tubal wall thereof and is used to support and fix the fiber element 212. The fiber element 212 transversely crosses two tubal sides of the conduit 35 and respectively penetrates through the corresponding notch 351 to engage with the liquid accumulator 37 in order for absorbing smoke liquid therefrom to facilitate atomizing of the heating wire 211.

The liquid accumulator 37 (as shown in FIGS. 3-4) is used to absorb and store smoke liquid filled in the smoke liquid reservoir 3 for facilitating the atomizer device 2 to atomize the smoke liquid afterwards. The liquid accumulator 37 is capable of absorbing and storing water like a sponge and is able to be made of any materials like cotton which is able to absorbing and isolate liquid. The liquid accumulator 37 is a hollow cylinder structure, and is sheathingly installed outside the conduit 35 and is snugly engaged with the outer wall of the conduit 35 for support. Two ends of the liquid accumulator 37 are respectively inserted into the annular inner chamber 317 of the seat 31 and the annular inner chamber 47 of the inhaling cover 4. A sidewall of the liquid accumulator 37 engages with the fiber element 212 so as to allow the smoke liquid permeating from the liquid accumulator 37 toward the fiber element 212 for absorption, and then being evaporated into smoke by the heating wire 211.

The positioning tube 39 (as shown in FIG. 3) is used to restrain a location of the atomizing device 21 on the conduit 35, and is an insulating hollow tube to snugly fit with the conduit 35. The positioning tube 39 is able to be made of plastic or fiber materials, such as glass fiber tubes. The positioning tube 39 is sheathingly installed at the outer wall of the conduit 35, and is interferentially engaged with the conduit 35. A bottom of the positioning tube 39 engages with the atomizing device 21 to prevent the atomizing device 21 from moving along an axial direction of the conduit 35.

Figure 9:
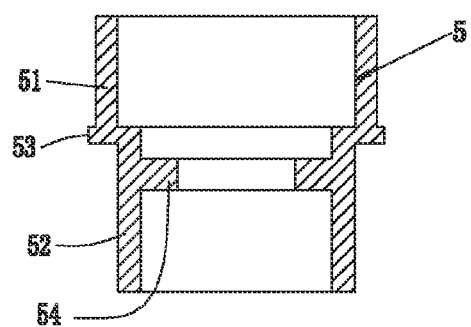
FIG. 9 is a cross-sectional view of a male connecting element of an electronic cigarette in accordance with the first embodiment of the present invention.

As shown in FIGS. 3-4 and 9, the male connecting element 5 is located at the second end 12 of the inhaling cylinder 1, and is shaped to correspondingly match with the inhaling cylinder 1. The male connecting element 5 is able to be made of magnetic materials which can be attracted by magnets, such as iron materials. The male connecting element 5 is inserted into the inhaling cylinder 1 to engage with the seat 31. The male connecting element 5 is substantially a hollow cylinder, and comprises a cylindrical upper portion 51 and a cylindrical lower portion 52. The upper portion 51 is connectively engaged with the inhaling cylinder 1, and the lower portion 52 is connectively engaged with the power unit 91. A positioning step 53 is formed at a cylindrical periphery of the male connecting element 5 between the upper portion 51 and the lower portion 52, and in the meantime, the positioning step 53 is used to engage with the power unit 91 and restrict relative locations thereof. An engaging ring 54 is formed at an inner wall of the lower portion 52 for installation of the first atomizing electrode 13 which adopts and uses the first insulating ring 14 to be installed inside the engaging ring 54.

Figure 5:
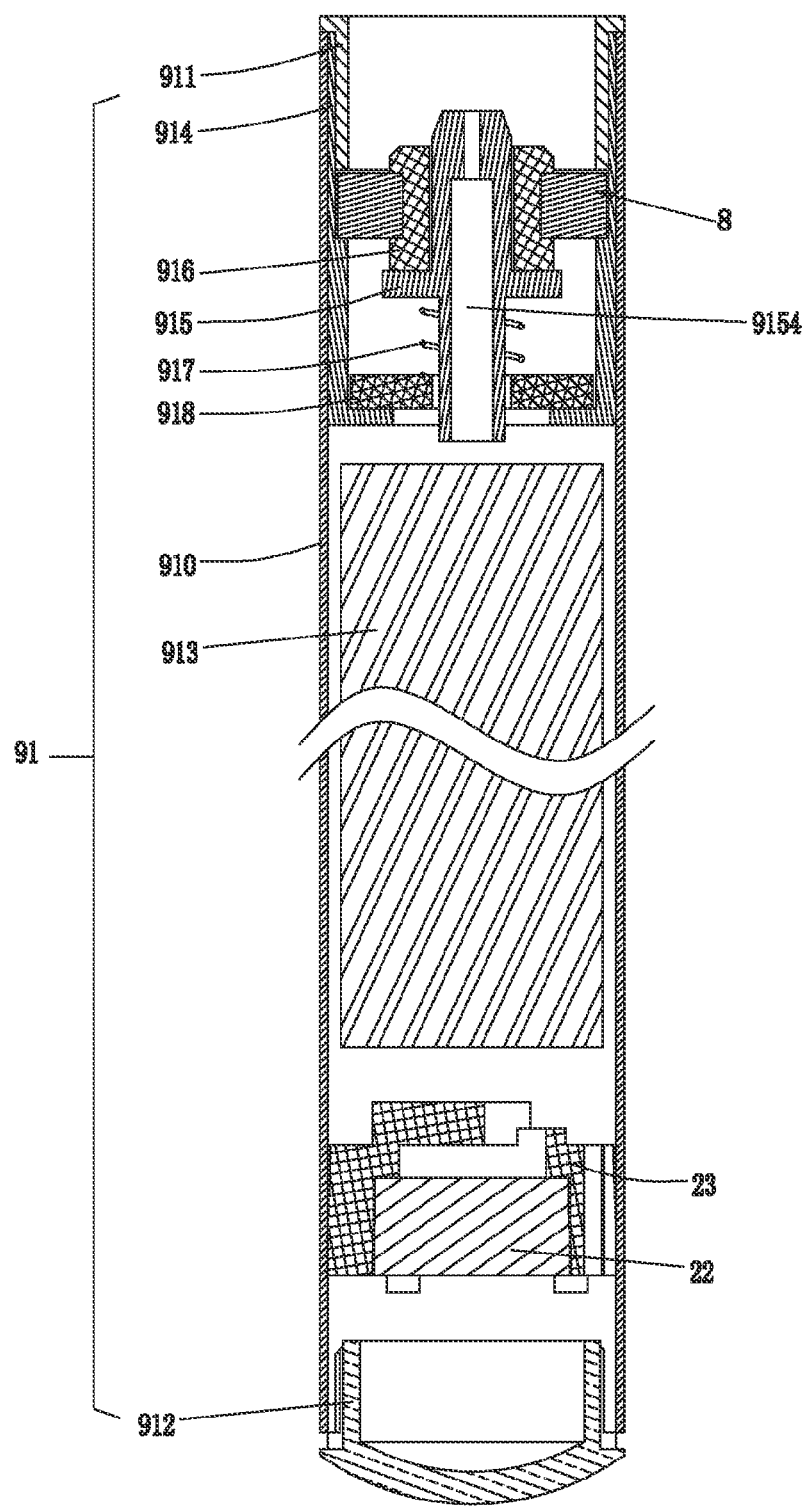
FIG. 5 is a cross-sectional view of a power unit of an electronic cigarette in accordance with the first embodiment of the present invention.
Figure 6:
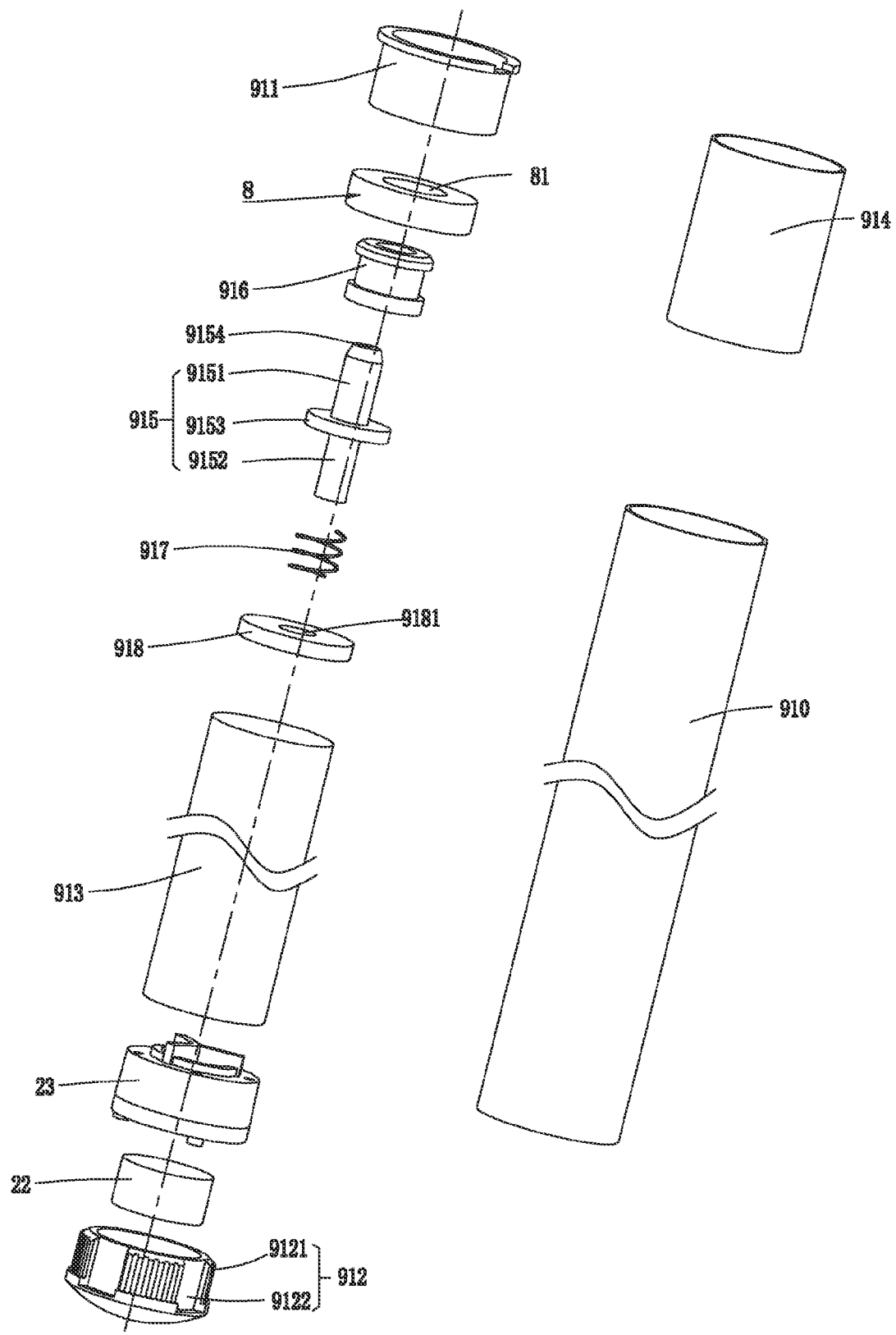
FIG. 6 is an exploded view of a power unit of an electronic cigarette in accordance with the first embodiment of the present invention.
Figure 7:
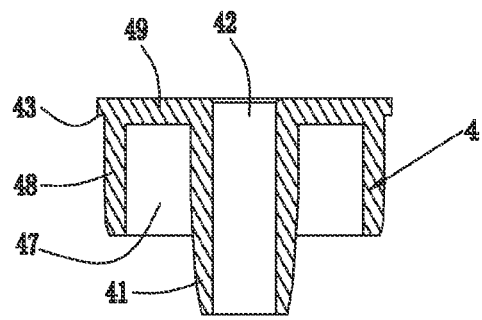
FIG. 7 is a cross-sectional view of an inhaling cover of an electronic cigarette in accordance with the first embodiment of the present invention.

As shown in FIGS. 5 and 6, the fixing sheath 914 is disposed in the power unit 91 to be a part of the power unit 91. The power unit 91 comprises a sleeve 910, the female connecting element 911 and a bottom cover 912 both of which are respectively disposed at two ends of the sleeve 910, a battery 913 accommodated in the sleeve 910, the fixing sheath 914 used for securing the female connecting element 911 in the sleeve 910, the first battery electrode 915 electrically connected with electrodes of the battery 913 (such as negative electrode), a second insulator 916, a flexible element 917 and an insulating pad 918. The permanent magnet 8 is further installed in the power unit 91 to magnetize the female connecting element 911 in order for attractively connecting with the male connecting element 5 by magnetism. In this embodiment, the permanent magnet 8 is a magnet, and is shaped as a ring to correspondingly match with the fixing sheath 914. A center of the permanent magnet 8 forms a fixation hole 81 for securing the first battery electrode 915.

Figure 10:
FIG. 10 is a cross-sectional view of a female connecting element of an electronic cigarette in accordance with the first embodiment of the present invention.

As shown in FIG. 10, the female connecting element 911 is made of magnetic materials, such as iron material, and matches the male connecting element 5. The female connecting element 911 is disposed at a top of the sleeve 910 and used for connecting the smoking unit 90 to the power unit 91. The female connecting element 911 is substantially a hollow cylinder, and comprises a cylindrical first connecting part 9111. A first chamber 9112 is defined inside the first connecting part 9111 in order to insertably connect and mate with the lower portion 52 of the male connecting element 5. A positioning step 9113 is disposed and extends outwardly from an outer wall of the first connecting part 9111 along a radial direction thereof in order for correspondingly engaging with sleeve 910. The female connecting element 911 is snugly fixed at an inner wall of the sleeve 910 via an outer wall of the first connecting part 9111. In this embodiment, the female connecting element 911 is used as another electrode of the battery 913 (such as positive electrode). The female connecting element 911 is snugly fixed inside the fixing sheath 914 in advance, and further snugly fixed against the inner wall of the sleeve 910 via the fixing sheath 914.

As shown is FIG. 6, the bottom cover 912 is installed at a bottom of the sleeve 910. The bottom cover 912 comprises a protrusive fringe 9121 used to snugly engage with the sleeve 910 and an air inlet 9122.

Figure 11:
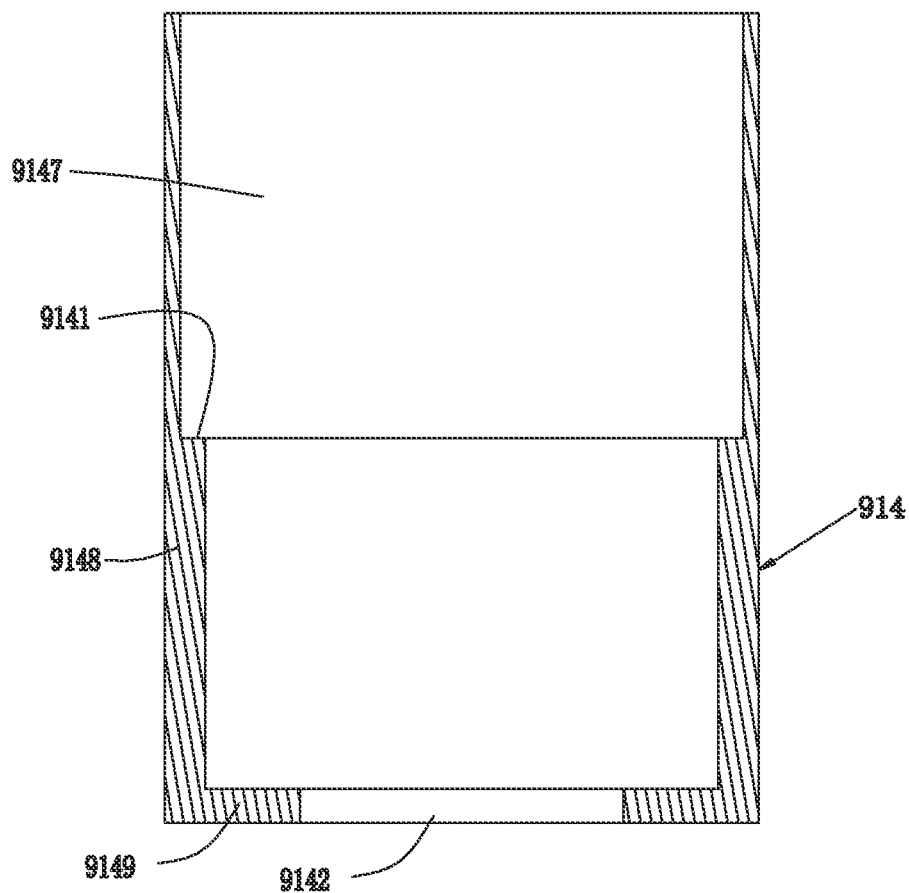
FIG. 11 is a cross-sectional view of a fixing sheath of an electronic cigarette in accordance with the first embodiment of the present invention.

As shown in FIG. 11, the fixing sheath 914 is cylindrical, and comprises a sidewall 9148, a bottom wall 9149 and an inner chamber 9147 formed and surrounded by the sidewall 9148 and the bottom wall 9149. The fixing sheath 914 is snugly secured at the inner wall of the sleeve 910 via an outer wall of the fixing sheath 914, and a positioning step 9141 is disposed at an inner wall of the fixing sheath 914 for supporting the permanent magnet 8. The bottom wall 9149 of the fixing sheath 914 comprises a through hole 9142. The permanent magnet 8 is disposed in the inner chamber 9147 of the fixing sheath 914 and the bottom of the permanent magnet 8 is supported on the positioning step 9141. The female connecting element 911 is inserted in the inner chamber 9147 of the fixing sheath 914 and engages with the top of the permanent magnet 8 in order to fix the permanent magnet 8. The fixing sheath 914 is an electrical conductor of metal material, and electrically contacts with the female connecting element 911 for electrical connection thereof.

As shown in FIGS. 5-6, the first battery electrode 915 is substantially cylindrical. A circular positioning step 9153 is formed at a central periphery thereof, and separates the first battery electrode 915 into an upper portion 9151 and a lower portion 9152. The second insulator 916 is sheathingly installed outside the upper portion 9151, and is snugly inserted and fixed in the fixation hole 81 of the permanent magnet 8 together with the upper portion 9151. An end of the second insulator 916 engages with a top surface of the positioning step 9153 for positioning in order to fix the first battery electrode 915 and the permanent magnet 8. A vent 9154 is formed and penetrates through the first battery electrode 915 along an axial direction thereof. The flexible element 917 is sheathingly installed at an outer wall of the lower portion 9152 of the first battery electrode 915. In this embodiment, the flexible element 917 is a spring. Two ends of the spring respectively engage with a bottom of the positioning step 9153 and the insulating pad 918. A pressing force generated by constricting the spring makes the first battery electrode 915 being held and secured in the second insulator 916 and unable to be loose. Since the fixing sheath 914 is an electric conductor and the spring sheathingly installed at the outer wall of the first battery electrode 915, the insulating pad 918 is further installed at a bottom wall of the fixing sheath 914 in order to prevent the first battery electrode 915 and the fixing sheath 914 from becoming short circuit. In details, the spring engages on the insulating pad 918 to avoid contact of the spring and the fixing sheath 914 leading to electrical conduction. A central through hole 9181 is installed at a center of the insulating pad 918. The lower portion 9152 of the first battery electrode 915 respectively penetrates through the central through hole 9181 of the insulating pad 918 and the through hole 9142 of the fixing sheath 914, and extends out of the fixing sheath 914 for facilitating air circulation.

When assembling the electronic cigarette 100 of the present invention, the male connecting element 5 is inserted into the female connecting element 911. Due to existence of the permanent magnet 8, the male connecting element 5 is magnetically attracted by and attached to the permanent magnet 8 to engage therewith. An attraction force between the male connecting element 5 and the female connecting element 911 also exist for realizing tight connection between the smoking unit 90 and the power unit 91. When dismantling the electronic cigarette 100, simply pulling out the power unit 91 by overcoming the attraction force will enable disassembly of the electronic cigarette 100. The above mentioned connective way facilitates convenient and efficient assembly and disassembly of the electronic cigarette 100. Before insertion of the male connecting element 5 of the electronic cigarette 100 for working, smoke liquid from the liquid accumulator 37 permeates toward and is stored in the fiber element 212. When working of the electronic cigarette 100 initiates, circuits for the heating wire 211 of the atomizing device 2 are electrically connected to power the heating wire 211 for heating. The smoke liquid stored in the fiber element 212 is heated by the heating wire 211, and atomized to turn to smoke. The smoke passes through the conduit 35 and is inhaled by smokers via the inhaling-cover vent 42 of the inhaling cover 4.

Figure 12:
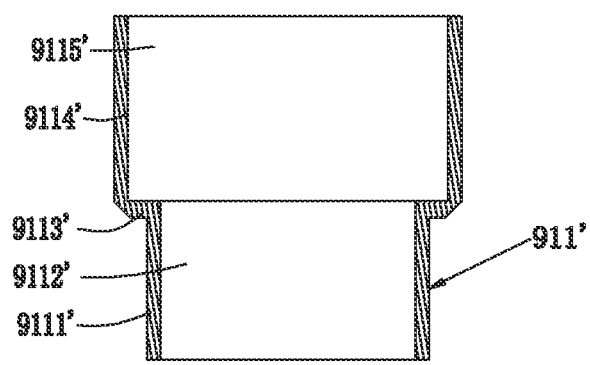
FIG. 12 is a cross-sectional view of a female connecting element of an electronic cigarette in accordance with the second embodiment of the present invention.
Figure 13:
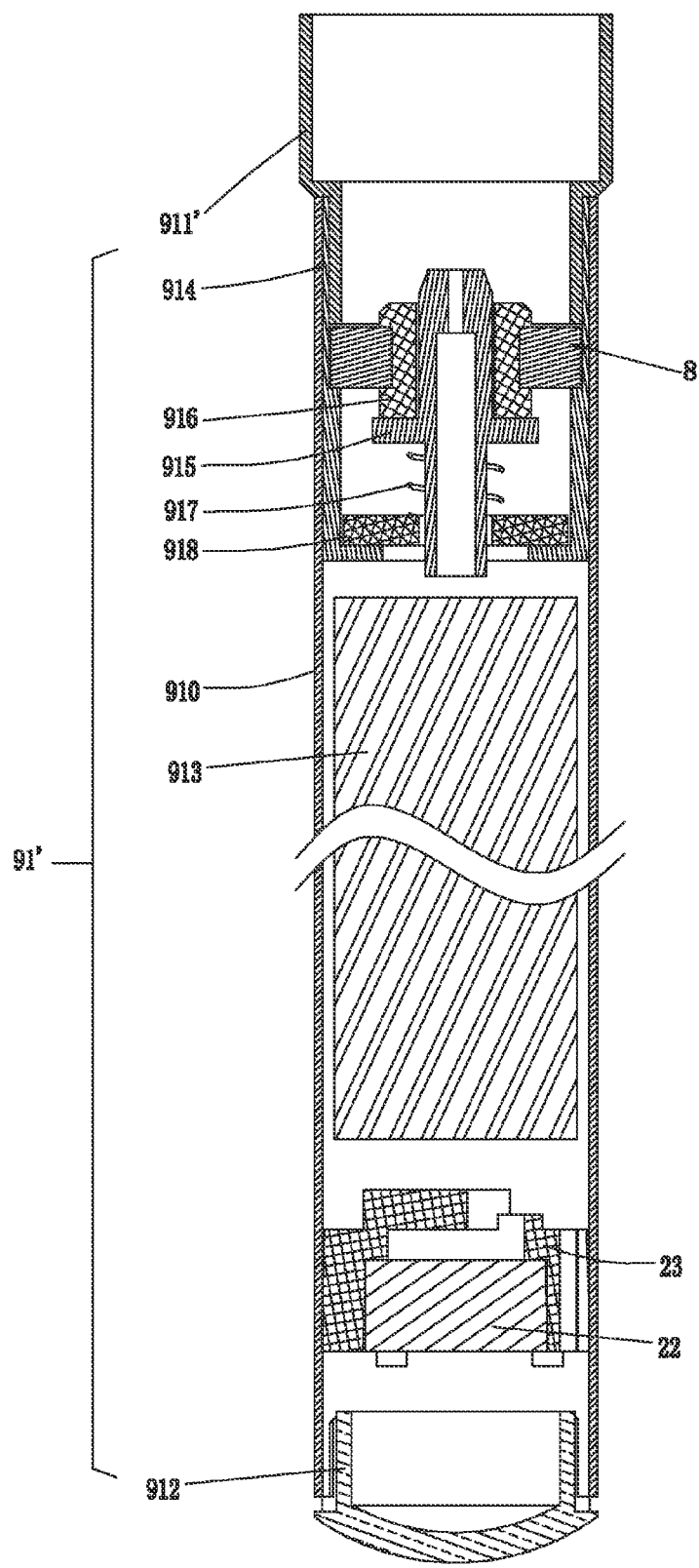
FIG. 13 is a cross-sectional view of a power unit of an electronic cigarette in accordance with the second embodiment of the present invention.

As shown in FIGS. 12-13, another type of a power unit 91' is provided in accordance with the second embodiment of the present invention. The structure of the power unit 91' is substantially the same as the power unit 91 of the first embodiment except a female connecting element 911' of the power unit 91'. The female connecting element 911' is substantially hollow and cylindrical, and comprises a cylindrical first connecting part 9111', and a first chamber 9112' formed inside the first connecting part 9111' and used to be insertedly connected and mated with the lower portion 52 of the male connecting element 5. A positioning step 9113' is disposed at and extends outwardly from an outer wall of the first connecting part 9111' along a radial direction thereof, and is used for correspondingly engaging with the sleeve 910. The female connecting element 911' is snugly fixed at the inner wall of the sleeve 910 via the outer wall of the first connecting part 9111'. The female connecting element 911' further comprises a second connecting part 9114' used for sheathingly engaging with the smoking unit 90. The second connecting part 9114' is cylindrical and is formed by starting from the positioning step 9113' and extending away from the first connecting part 9111' along an axial direction thereof of. The second connecting part 9114' communicates with the first connecting part 9111', and forms a cylindrical second chamber 9115' therein for accommodating the second end 12 of the inhaling cylinder 1. An inner wall of the second connecting part 9114' and an outer wall of the inhaling cylinder 1 are interferentially engaged with each other so as to make fixed and reliable connection between the smoking unit 90 and the power unit 91'.

Accounting to the electronic cigarette 100 in accordance with the embodiments of the present invention, the permanent magnet 8 is disposed in the power unit 91. Understandably, the permanent magnet 8 disposed in the smoking unit 90 also enable to realize a magnetic connection of the smoking unit 90 and the power unit 91. For example, the permanent magnet 8 is disposed in the male connecting element 5. The male connecting element 5 is able to generate magnetic attraction because of existence of the permanent magnet 8, and is able to be inserted into the power unit 91 for attachably connection therewith. The electronic cigarette 100 in accordance with the embodiments of the present invention is alternatively provided as following. The male connecting element 5 of the smoking unit 90 and the female connecting element 911 of the power unit 91 are both equipped with the permanent magnet 8, and the two permanent magnets 8 of the male connecting element 5 and the female connecting element 911 are magnetically attracted to each other when the male connecting element 5 and the female connecting element 911 are connected with each other.

The above mentioned is only exemplary embodiments of the present invention. It should be noted, for persons of ordinary skill in this art field, improvements and modifications within the spirit of the present invention can be further made, and such improvements and modifications should be seemed to be included in the claimed scope of the present invention.

What is claimed is:

1. An electronic cigarette, comprising a smoking unit and a power unit, wherein the smoking unit attachably connects with the power unit as a unitary member by magnetism;
   a connecting end of the smoking unit and a corresponding connecting end of the power unit respectively comprise a connecting element which is made of iron material, a permanent magnet is disposed in at least one of the connecting end of the smoking unit and the corresponding end of the power unit, and the connecting element of the connecting end of the smoking unit and the connecting element of the corresponding connecting end of the power unit are removably and insertedly connected to each other, and engaged with each other via an attractive force of the permanent magnet;
   a bottom of the permanent magnet is supported by a flexible element.

2. The electronic cigarette as claimed in claim 1, wherein ends of the two connecting elements are attracted to each other and one of the ends of the two connecting elements abuts against a top of the permanent magnet, the permanent magnet is configured to be fixed in the connecting end of the smoking unit or the corresponding end of the power unit by an iron fixing sheath.

3. The electronic cigarette as claimed in claim 2, wherein the connecting elements are cylindrical, and the permanent magnet is a ring structure, a first battery electrode is insertedly disposed in a center of the ring structure of the permanent magnet, and an insulator is disposed between the first battery electrode and the permanent magnet.

4. The electronic cigarette as claimed in claim 3, wherein the fixing sheath is cylindrical, and comprises a sidewall, a bottom wall, and an inner chamber formed and surrounded by the sidewall and the bottom wall, the fixing sheath is snugly secured at an inner wall of the connecting end of the smoking unit or the corresponding connecting end of the power unit via an outer wall of the fixing sheath, a positioning step of the fixing sheath is formed at an inner wall of the fixing sheath for supporting the permanent magnet, the permanent magnet is installed in the inner chamber of the fixing sheath and the bottom of the permanent magnet is supported on the positioning step of the fixing sheath, an end of one of the connecting element and the corresponding connecting element is inserted into the fixing sheath and engages with a top of the permanent magnet in order to fix the permanent magnet, the bottom wall of the fixing sheath comprises a through hole.

5. The electronic cigarette as claimed in claim 4, wherein the connecting element of the corresponding connecting end of the power unit is a female connecting element, correspondingly, a male connecting element is the connecting element of the connecting end of the smoking unit, the permanent magnet is disposed at the corresponding connecting end of the power unit, the first battery electrode insertedly disposed in the center of the permanent magnet is the first battery electrode of the power unit, and the female connecting element is a second battery electrode of the power unit.

6. The electronic cigarette as claimed in claim 5, wherein the female connecting element is fixed at the corresponding connecting end of the power unit via the iron fixing sheath, and the fixing sheath is insertedly installed at an inner wall of the corresponding connecting end of the power unit, and the permanent magnet is fixed in the fixing sheath.

7. The electronic cigarette as claimed in claim 5, wherein the female connecting element comprises a cylindrical first connecting part, a first chamber is defined inside the first connecting part in order to insertably connect and mate with the male connecting element, a positioning step of the first connecting part is disposed and extends outwardly from an outer wall of the first connecting part along a radial direction of the first connecting part in order for snugly matching with the corresponding connecting end of the power unit, and the female connecting element is snugly fixed at the inner wall of the corresponding connecting end of the power unit via the outer wall of the first connecting part.

8. The electronic cigarette as claimed in claim 7, wherein the female connecting element further comprises a second connecting part used to insertedly connect with the connecting end of the smoking unit, the second connecting part is cylindrical and is formed by starting from the positioning step of the first connecting part and extending away from the first connecting part along an axial direction thereof, the second connecting part communicates with the first connecting part and forms a cylindrical second chamber therein for accommodating the connecting end of the smoking unit, an inner wall of the second connecting part and an outer wall of the connecting end of the smoking unit are interferentially engaged with each other.

9. The electronic cigarette as claimed in claim 4, wherein the male connecting element comprises a cylindrical upper portion and lower portion, the upper portion of the male connecting element is used to connectively engage with the connecting end of the smoking unit, and the lower portion of the male connecting element is used to connectively engage with the female connecting element, a positioning step of the male connecting element is formed between the upper portion and the lower portion of the male connecting element by extending outwards along a radial direction of the male connecting element, and is used to engage with the connecting end of the smoking unit, the positioning step of the male connecting element is used to engage with the female connecting element at the same time for restricting relative locations thereof, an engaging ring is formed at an inner wall of the lower portion for installation of a first atomizing electrode of the smoking unit, the first atomizing electrode of the smoking unit is secured in the engaging ring via an insulating piece, a vent is formed at a center of the smoking unit and penetrates through the smoking unit along an axial direction thereof, and the male connecting element is used as a second atomizing electrode of the smoking unit.

10. The electronic cigarette as claimed in claim 5, wherein a fixation hole is formed at a center of the permanent magnet and is used to install the first battery electrode therein, the first battery electrode is fixed in the fixation hole via an insulator, the first battery electrode is cylindrical, a circular positioning step of the first battery electrode is formed at a central periphery of the first battery electrode and separates the first battery electrode into an electrode upper portion and an electrode lower portion, an electrode vent is further formed and penetrates through the first battery electrode along an axial direction thereof.

11. The electronic cigarette as claimed in claim 10, wherein the insulator is sheathingly installed outside the electrode upper portion of the first battery electrode, and is snugly inserted and fixed in the fixation hole of the permanent magnet together with the electrode upper portion, a bottom of the insulator engages with a top surface of the positioning step of the first battery electrode for positioning in order to fix the positioning step of the first battery electrode at a location spaced from the bottom of the permanent magnet.

12. The electronic cigarette as claimed in claim 10, wherein the electrode lower portion of the first battery electrode is electrically insulated from the fixing sheath via an insulating pad, the insulating pad is disposed at the bottom wall of the fixing sheath, and a central through hole is formed at a center of the insulating pad and penetrates through the insulating pad along an axial direction thereof.

13. The electronic cigarette as claimed in claim 12, wherein the flexible element is sheathingly installed at an outer wall of the electrode lower portion of the first battery electrode of the power unit, both ends of the flexible element respectively engage with the positioning step of the first battery electrode and the insulating pad, a pressing force generated by constricting the flexible element is used to tightly engage the first battery electrode, the permanent magnet, the female connecting element, and the fixing sheath together, and to further make the permanent magnet elastically engaging with the female connecting element.

14. The electronic cigarette as claimed in claim 12, wherein the electrode lower portion of the first battery electrode penetrates respectively through the central through hole of the insulating pad and the through hole of the fixing sheath, and extends out of the bottom wall of the fixing sheath.

* * * * *